(12) United States Patent
Hering et al.

(10) Patent No.: US 9,579,662 B2
(45) Date of Patent: Feb. 28, 2017

(54) CONDENSATION-EVAPORATOR NANOPARTICLE CHARGER

(71) Applicant: Aerosol Dynamics Inc., Berkeley, CA (US)

(72) Inventors: Susanne Vera Hering, Berkeley, CA (US); Steven Russel Spielman, Oakland, CA (US); Gregory Stephen Lewis, Berkeley, CA (US)

(73) Assignee: AEROSOL DYNAMICS INC., Berkeley, CA (US)

( * ) Notice: Subject to any disclaimer, the term of this patent is extended or adjusted under 35 U.S.C. 154(b) by 177 days.

(21) Appl. No.: 14/043,662

(22) Filed: Oct. 1, 2013

(65) Prior Publication Data

US 2014/0029154 A1   Jan. 30, 2014

Related U.S. Application Data

(63) Continuation-in-part of application No. 13/218,393, filed on Aug. 25, 2011, now Pat. No. 8,801,838.
(Continued)

(51) Int. Cl.
*B01D 53/00* (2006.01)
*B03C 3/38* (2006.01)
(Continued)

(52) U.S. Cl.
CPC ............. *B03C 3/38* (2013.01); *B01D 5/0009* (2013.01); *B01D 53/002* (2013.01);
(Continued)

(58) Field of Classification Search
CPC .......... G01M 15/102; B01D 2257/504; B01D 53/002; B01D 53/1475; B01D 5/0009;
(Continued)

(56) References Cited

U.S. PATENT DOCUMENTS 2,042,095 A   5/1936   Grant, Jr.
2,684,008 A   7/1954   Vonnegut
(Continued)

FOREIGN PATENT DOCUMENTS

DE   4008348 A1   9/1991
EP   0462413 A2   12/1991
(Continued)

OTHER PUBLICATIONS

Leaitch, R., et al., "The Diffusion Tube: A Cloud Condensation Nucleus Counter for Use Below 0.3% Supersaturation," Journal of Aerosol Science., vol. 13, No. 4, 1982, 23 pages.
(Continued)

*Primary Examiner* — Dung H Bui
(74) *Attorney, Agent, or Firm* — Vierra Magen Marcus LLP

(57) ABSTRACT

A particle charging method and apparatus are provided. An ion source is applied to a particle laden flow. The flow is introduced into a container in a laminar manner. The container has at least a first section, a second section and a third section. The first section includes wetted walls at a first temperature. A second section adjacent to the first section has wetted walls at a second temperature T2 greater than the first temperature T1. A third section adjacent to the second section has dry walls provided at a temperature T3 equal to or greater than T2. Additional water removal and temperature conditioning sections may be provided.

19 Claims, 5 Drawing Sheets

Related U.S. Application Data

(60) Provisional application No. 61/709,949, filed on Oct. 4, 2012, provisional application No. 61/402,348, filed on Aug. 27, 2010.

(51) Int. Cl.

| | | |
|---|---|---|
| B01D 53/14 | (2006.01) | |
| B01D 5/00 | (2006.01) | |
| G01N 15/06 | (2006.01) | |
| G01N 15/14 | (2006.01) | |
| G01N 15/00 | (2006.01) | |

(52) U.S. Cl.
CPC ....... B01D 53/1475 (2013.01); G01N 15/065 (2013.01); *B01D 2257/504* (2013.01); *G01N 2015/0038* (2013.01); *G01N 2015/1481* (2013.01)

(58) Field of Classification Search
CPC ........ Y02T 10/47; B03C 3/38; G01N 15/065; G01N 2015/0038; G01N 2015/1481
USPC .... 95/228, 288, 149, 227; 96/243, 322, 413; 261/128; 73/28.05, 28.01, 28.04, 31.02, 73/31.03, 863.12, 863.21, 23.31; 62/617, 62/640, 657; 356/37, 339
See application file for complete search history.

(56) References Cited

U.S. PATENT DOCUMENTS

| | | | |
|---|---|---|---|
| 2,721,495 A | 10/1955 | Schaefer | |
| 3,011,387 A | 12/1961 | Johnson | |
| 3,011,390 A | 12/1961 | Van Luik, Jr. | |
| 3,037,421 A | 6/1962 | Bigelow et al. | |
| 3,592,546 A | 7/1971 | Gussman | |
| 3,632,210 A | 1/1972 | Rich | |
| 3,694,085 A | 9/1972 | Rich | |
| 3,738,751 A | 6/1973 | Rich | |
| 3,806,248 A | 4/1974 | Sinclair | |
| 3,825,790 A * | 7/1974 | Bacal .................. | G21K 1/14 313/362.1 |
| 3,890,046 A | 6/1975 | Hart et al. | |
| 4,293,217 A | 10/1981 | Bird, Jr. et al. | |
| 4,449,816 A | 5/1984 | Kohsaka et al. | |
| 4,761,074 A | 8/1988 | Kohsaka et al. | |
| 4,790,650 A | 12/1988 | Keady | |
| 4,792,199 A | 12/1988 | Borden | |
| 4,868,398 A | 9/1989 | Mulcey et al. | |
| 4,950,073 A | 8/1990 | Sommer | |
| 4,967,187 A | 10/1990 | Dumas et al. | |
| 5,011,281 A | 4/1991 | Harris | |
| 5,026,155 A | 6/1991 | Ockovic et al. | |
| 5,098,657 A | 3/1992 | Blackford et al. | |
| 5,118,959 A | 6/1992 | Caldow et al. | |
| 5,176,723 A | 1/1993 | Liu et al. | |
| 5,239,356 A | 8/1993 | Hollander et al. | |
| 5,278,626 A | 1/1994 | Poole et al. | |
| 5,519,490 A | 5/1996 | Nakata et al. | |
| 5,659,388 A | 8/1997 | Scheer et al. | |
| 5,675,405 A | 10/1997 | Schildmeyer et al. | |
| 5,872,622 A | 2/1999 | Schildmeyer et al. | |
| 5,903,338 A | 5/1999 | Mavliev et al. | |
| 6,330,060 B1 | 12/2001 | Flagan et al. | |
| 6,469,780 B1 | 10/2002 | McDermott et al. | |
| 6,498,641 B1 | 12/2002 | Schildmeyer | |
| 6,529,272 B2 | 3/2003 | Flagan et al. | |
| 6,567,157 B1 | 5/2003 | Flagan et al. | |
| 6,712,881 B2 | 3/2004 | Hering et al. | |
| 6,829,044 B2 | 12/2004 | Liu | |
| 6,980,284 B2 | 12/2005 | Ahn et al. | |
| 7,298,486 B2 * | 11/2007 | Wang .................. | G01N 15/0266 324/71.4 |
| 7,719,683 B2 | 5/2010 | Ahn | |
| 7,724,368 B2 | 5/2010 | Ahn | |
| 7,736,421 B2 | 6/2010 | Hering et al. | |
| 7,828,273 B2 | 11/2010 | Molter et al. | |
| 7,988,135 B2 | 8/2011 | Molter et al. | |
| 8,072,598 B2 | 12/2011 | Ahn | |
| 2003/0082825 A1 | 5/2003 | Lee et al. | |
| 2004/0020362 A1 | 2/2004 | Hering et al. | |
| 2006/0126056 A1 | 6/2006 | Roberts et al. | |
| 2006/0146327 A1 * | 7/2006 | Wang .................. | G01N 15/0266 356/338 |
| 2006/0156791 A1 * | 7/2006 | Tikkanen et al. ............ | 73/23.33 |
| 2008/0041138 A1 * | 2/2008 | Marra .......................... | 73/31.02 |
| 2008/0083274 A1 | 4/2008 | Hering et al. | |
| 2008/0137065 A1 * | 6/2008 | Oberreit et al. ............... | 356/37 |
| 2008/0144003 A1 | 6/2008 | Blackford et al. | |
| 2010/0180666 A1 | 7/2010 | Huetter et al. | |
| 2011/0095095 A1 | 4/2011 | Hering et al. | |
| 2012/0048112 A1 | 3/2012 | Hering et al. | |

FOREIGN PATENT DOCUMENTS

| | | |
|---|---|---|
| EP | 2208983 A2 | 7/2010 |
| WO | WO8908245 A1 | 9/1989 |
| WO | 2008058182 A2 | 5/2008 |

OTHER PUBLICATIONS

Choi, Youngjoo, et al., "An improved method for chargin submicron and nanoparticles with uniform charging pertormace," Aerosol Science and Technology, vol. 41, Issue 3, pp. 259-265, Jan. 2007.
Han, B.W., et al., "Enhanced unipolar charging of concentraion-enriched particles using water-based condensational growth," Journal of Aerosol Science, vol. 39, Issue 9, pp. 770-784, Sep. 2008.
Kim, D. S., et al., "Control of nanoparticle charge via condensation magnification," Journal of Aerosol Science, vol. 37, Issue 12, pp. 1876-1882, Dec. 2006.
Suh, J. B., et al., "A method for enhanced charging of nanoparticles via condensation magnification," Journal of Aerosol Science, vol. 36, Issue 10, pp. 1183-1193, Oct. 2005.
Notification of Transmittal of the International Search Report and the Written Opinion, mailed Jan. 16, 2014, in International Patent Application No. PCT/US2013/063082 filed Oct. 2, 2013.
Hering, Susanne V., et al., "A Method for Particle Size Amplification by Water Condensation in a Laminar, Thermally Diffusive Flow," Aerosol Science and Technology, 39: 428-436, Mar. 2005, 9 pages.
Hering, Susanne V., et al., "A Laminar-Flow, Water-Based Condensation Particle Counter (WCPC)," Aerosol Science and Technology, 39: 659-672, Apr. 2005, 14 pages.
Stolzenburg, Mark R., et al., "An Ultrafine Aerosol Condensation Nucleus Counter," Aerosol Science and Technology, 14: 48-65, Jan. 1991, 19 pages.
Invitation to Pay Additional Fees and Communication Relating to the Results of the Partial International Search dated Nov. 4, 2011, in International Patent Application No. PCT/US2011/049391 filed Aug. 26, 2011.
Seager, Spencer L., et al., "Temperature Dependence of Gas and Vapor Diffusion Coeeficients," Journal of Chemical & Engineering Data, vol. 8, No. 2, Apr. 1, 2963, pp. 168-169.
English Abstract of European Publication No. EP 0462413 published Dec. 27, 1991.
English Abstract of European Publication No. EP 2208983 published Jul. 21, 2010.
International Search Report dated Jan. 18, 2012, International Application No. PCT/US2011/049391.
Office Action dated Apr. 9, 2013, U.S. Appl. No. 13/218,393, filed Aug. 25, 2011.
Response to Office Action dated Jul. 9, 2013, U.S. Appl. No. 13/218,393, filed Aug. 25, 2011.
Office Action dated Aug. 30, 2013, U.S. Appl. No. 13/218,393, filed Aug. 25, 2011.
International Preliminary Report on Patentability, mailed Apr. 16, 2015, in International Patent Application No. PCT/US2013/063082 filed Oct. 2, 2013.

(56) References Cited

OTHER PUBLICATIONS

International Preliminary Report on Patentability, mailed Apr. 16, 2015, in International Patent Application No. PCT/US2013/063076 filed Oct. 2, 2013.
Notification of Transmittal of the International Search Report and the Written Opinion, mailed Apr. 25, 2014, in International Patent Application No. PCT/US2013/063076 filed Oct. 2, 2013.
McMurry, Peter H., "The History of Condensation Nucleus Counters," Aerosol Science and Technology, Oct. 2000, 26 pages.
Stolzenburg, Mark R., et al., "An Ultrafine Aerosol Condensation Nucleus Counter," Aerosol Science and Technology, Sep. 17, 2007, 19 pages.
Response to Office Action dated Mar. 14, 2016 in U.S. Appl. No. 14/043,455, filed Oct. 1, 2013.
Restriction dated Jun. 9, 2015, in U.S. Appl. No. 14/043,455, filed Oct. 1, 2013.
Amendment dated Aug. 10, 2015, in U.S. Appl. No. 14/043,455, filed Oct. 1, 2013.
Office Action dated Oct. 15, 2015, in U.S. Appl. No. 14/043,455, filed Oct. 1, 2013.
Final Office Action dated Sep. 29, 2016, in U.S. Appl. No. 14/043,455, filed Oct. 1, 2013.
Amendment dated Sep. 8, 2016, in U.S. Appl. No. 14/043,455, filed Oct. 1, 2013.

* cited by examiner

CONDENSATION-EVAPORATOR NANOPARTICLE CHARGER

CLAIM OF PRIORITY

This application is a continuation in part of U.S. patent application Ser. No. 13/218,393 filed on Aug. 25, 2011 entitled, "ADVANCED LAMINAR FLOW WATER CONDENSATION TECHNOLOGY FOR ULTRAFINE PARTICLES", which claims priority to U.S. Provisional Application No. 61/402,348 filed Aug. 27, 2010, which applications are hereby incorporated by reference in their entirety.

This application claims priority to U.S. Provisional Application Ser. No. 61/709,949 filed Oct. 4, 2012, inventors Susanne V. Hering, Steven R. Spielman, Gregory S. Lewis, which application is hereby incorporated by reference in its entirety.

GOVERNMENT LICENSE RIGHTS

This technology was made with government support under Grant No. DE-SC0004643 and DE-SC00009644 from the US Department of Energy. The government has certain rights in the technology.

BACKGROUND

Electrostatic deposition and electrical mobility size separation of airborne particles are widely used techniques for the collection or analysis of airborne particles. These methods require that the particles to be collected or analyzed carry an electric charge. However, for very small particles with diameters less than about 50 nm, adding an electrical charge is difficult. In this size range exposure to a bipolar ion source provides singly charged particles, but the charging efficiency is low. For particles with diameters of 50 nm, just 17% of the particles will acquire a positive charge, with an approximately equal number acquiring a negative charge. At 10 nm the fraction of particles charged with a single polarity is ~4%, and at 3 nm this drops to less than 2%. Unipolar charging can improve charging efficiencies for particles above about 10 nm, but it also becomes ineffective at smaller particle sizes.

One technique that has been used to increase the charging efficiency of these small particles is condensation-enhanced particle charging, wherein the particles are grown through condensation, charged and re-evaporated. Some prior art techniques have used butanol condensation to prepare highly charged particles in the 10-30 nm size range. Others have used condensation of glycol to enhance the charging of sub-20 nm particles. Still others have explored this approach with water condensation, albeit for larger (80-130 nm) particles. Limitations of these existing methods are: (1) the contamination of the particle through the use of organic materials as the condensing vapor, (2) addition of multiple electrical charges to each particle, and (3) inability to charge particles below about 10 nm.

SUMMARY

A system and method to provide efficient, low-level electrical charging of particles in the sub-100 nm size range is disclosed. This method uses an ion source coupled to a laminar flow water condensation and evaporation cell. Ions are introduced together with a particle-laden flow into a water condensation and evaporation device. In the presence of the ions, particles grow through water condensation, collide with the ions to become charged, and then quickly evaporate to return the particle to near its original size. The dried particle retains the electrical charge acquired as a droplet, leaving a higher fraction of charged particles than entered the system. The time as a droplet can be short, less than 200 milliseconds. With this short residence time the opportunities for chemical artifacts are minimized. The process occurs in a laminar flow, wherein the saturation ratios can be controlled, and calculated.

A particle charging method and apparatus are provided. An ion source is applied to a particle laden flow. The flow is introduced into a container in a laminar manner. The container has at least a first section, a second section and a third section. The first section includes wetted walls at a first temperature. A second section adjacent to the first section has wetted walls at a second temperature T2 greater than the first temperature T1. A third section adjacent to the second section has dry walls provided at a temperature T3 equal to or greater than T2. Additional water removal and temperature conditioning sections may be provided.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Technology is provided for the placement of electrical charge on ultrafine, airborne particles. The condensation-evaporator nano-particle charging technology described herein places a controlled electrical charge on ultrafine and nanometer sized particles, generally those with diameters in the range from a few nanometers to a few hundred nanometers. This charging method uses an ion source in conjunction with a laminar flow, water condensation and droplet evaporator system. The ion source can be either a unipolar source, such as created through corona wire discharge, or a bipolar source, such as obtained with radioactive sources or soft-x-rays. The condensation-evaporator system is a multistage device with a two stage condenser as described in U.S. patent application Ser. No. 13/218,393, and which is specifically incorporated herein by reference.

Figure 1:
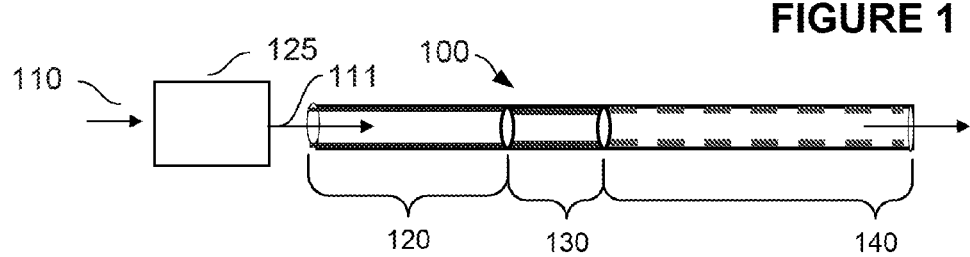
FIG. 1 is a schematic of a nanoparticle condensation charger in accordance with the present technology.

With reference to FIG. 1, the particle-laden airflow 110 passes through the ion source 125, and into the condensation-evaporator system 100. Ions are added to the particle laden flow by the ion source, and carried with the flow 111 into the condensation-evaporator. This ion source may be a bipolar source, such as is achieved with soft x-Rays or with a Po-210 or Kr-85 source. It could also be a unipolar ion source, or a flow with a high concentration of ions that is mixed with the flow 110. System 100 includes a first stage 120 generally referred to as a "conditioner." The second stage 130 and third stage 140, referred to as the "initiator" and "evaporator", respectively, form a two-part condenser, as described in U.S. patent application Ser. No. 13/218,393. The conditioner 120 is generally operated with slightly cooled walls, and is used to condition the flow 110 to near the temperature of the conditioner walls, with a relative humidity near 100%. The second, "initiator" stage 130 has walls which are maintained warmer than that of the conditioner 120. The third, evaporator stage 140 is operated warmer than the initiator stage 130. As the cooler flow from the conditioner enters the warm, wet walled initiator section, water vapor diffuses from the walls into the cooler flow. Likewise the flow slowly warms. Yet, because of its high diffusion constant relative to the thermal diffusivity of air, water vapor diffuses more quickly. As a result, the flow becomes supersaturated, with its peak supersaturation along the centerline of the flow.

Particles larger than a certain size grow through condensation of water vapor to form droplets. Typically, this size is in the range of 3 nm to 10 nm. The droplets that are formed are several hundred nanometers in diameter. Ions that have been carried with the flow 111 attach to the droplet-encapsulated particles, creating an electrically charged droplet. Because the ion attachment is a strong function of particle size, the ion attachment to the droplets is much more efficient than were the particles not enlarged through condensation. Once charged, the droplets are evaporated by lowering the relative humidity in the flow to less than 100%. Experimental data shows that upon evaporation, the particles return to near their original size while retaining the electrical charge acquired as droplets. By operating the condensation system at saturation ratios in excess of 1, for example in the range of 1.2 to 1.8, it is possible to activate condensational growth on particles as small as 3 to 10 nm in diameter. For these small particles, the condensation-evaporation system facilitates much more efficient production of charged particles than is possible through direct exposure to an ion source.

The condensation-evaporator system illustrated in FIG. 1 consists of a conditioner 120, an initiator 130 and an equilibrator 140. The walls of the conditioner 120 and of the initiator 130 are actively wetted, as can be done using a wetted wick material lining the walls. The temperature T1 of the walls of the conditioner 120, is lower than the temperature T2 of the walls of the initiator 130. The walls of the equilibrator 140 are dry, and held at temperature T3 which is higher than, or equal to T2. The geometry of the system can be cylindrical, or it can consist of parallel plates. The flow enters the conditioner 120, and then flows through the initiator 130 and evaporator 140. The volumetric flow rate is constrained to producing a predominantly laminar flow. A predominantly laminar flow for a cylindrical geometry means the flow Reynolds number is generally below 2000. Additionally, the volumetric flow is sufficient to minimize buoyancy effects, corresponding to a value of the Froude number greater than 1. The Froude number describes the relative magnitude of forced to buoyancy-driven convection, and is defined by $Fr=(\rho V^2)/(\Delta \rho g L)$, where V is the characteristic velocity for forced convection, $\Delta \rho$ is the change in air density due to temperature difference, g is the gravitational constant and L is the characteristic distance. For a cylinder, this characteristic distance scales as the tube radius. For flow through a tube of the order of 1 to 2 L/min, with a temperature difference between successive stages of less than 50° C., these criteria can both be met through use of tube diameters of less than about 0.7 cm.

Again with reference to FIG. 1, the conditioner 120 serves to bring the temperature of the flow 111 entering the initiator 130 to a known value, and to regulate the relative humidity to be at, or near 100% at the conditioner wall temperature. The initiator 130 that follows the conditioner 120 is generally a shorter length than the conditioner, with walls that are warmer than those of the conditioner 120. Like the conditioner 120 the walls of the initiator 130 are also wetted. The evaporation of water from the wetted walls of the initiator 130 supplies the water vapor necessary to create supersaturation necessary for particle activation. Because the entering flow is cooler than the initiator wall temperature, and because water vapor diffuses more quickly than the carrier gas (generally air), the flow becomes supersaturated. This supersaturation activates the condensational growth on small particles, as described by U.S. patent application Ser. No. 13/218,393. However, the initiator does not provide sufficient time for droplet growth. Most of the droplet growth and the droplet evaporation occur in the warm, dry-walled "evaporator" stage 140. This dryer stage has dry walls that are as warm, or warmer than the walls of the initiator. The evaporator raises the temperature of the flow without introducing additional water vapor, thereby reducing the saturation.

Figure 2:
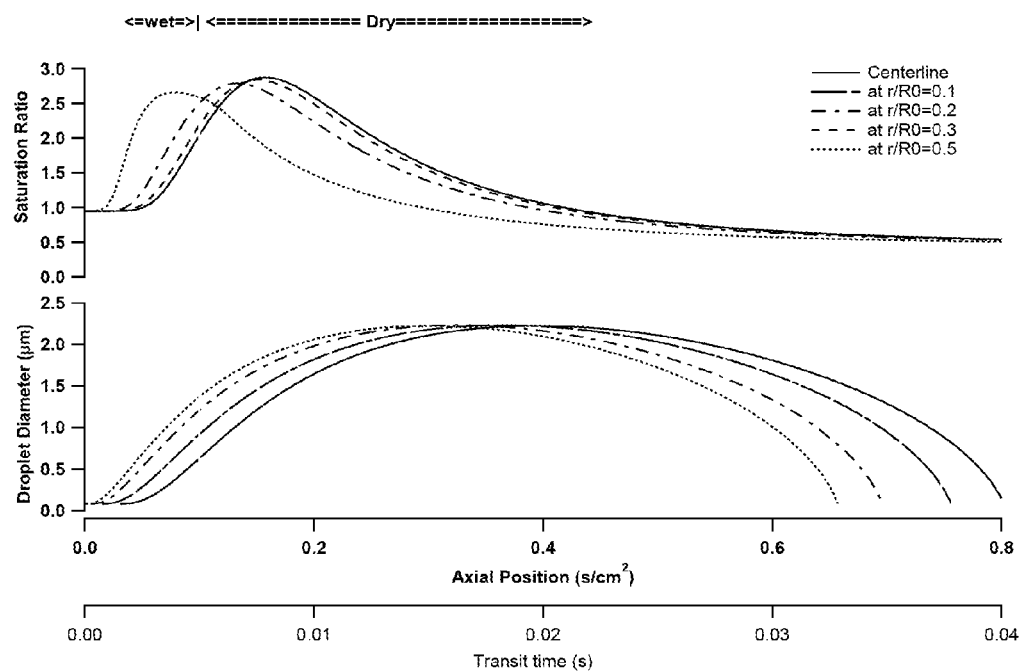
FIG. 2 is a graph of the calculated saturation ratio (top) and droplet diameter (bottom) as a function of axial position for a system operated to produce saturations sufficient to activate 3 nm particles.

FIG. 2 is a graph of the calculated saturation ratio (top) and droplet diameter (bottom) as a function of axial position for a system 100 operated to produce saturations sufficient to activate 3 nm particles. In this graph the primary abscissa is the axial position divided by the volumetric flow rate, in units of s/cm2. The secondary abscissa shows the corresponding residence time when utilizing a cylindrical geometry with an internal diameter of 2.5 mm.

Shown in FIG. 2 is the evolution of the saturation ratio and droplet diameter along several radial trajectories, from the center line (r/R0=0) to the halfway point (r/R0=0.5), where R0 is the radius of the tube. The water vapor supersaturation is created as a result of the transport of water vapor from the warm, wetted walls into the colder entering flow. Because the water molecule is smaller than the constituent molecules in air, the water vapor diffuses more quickly than the sensible heat, creating a region of water vapor supersaturation. This process produces controlled, calculable supersaturations. The maximum supersaturation occurs along the centerline, which handles the maximum of the flow.

With reference to FIG. 2, note that the maximum supersaturation occurs at, or just past the exit of the initiator. This is because the water vapor that contributes to the supersaturation requires time, and therefore distance, to reach the centerline. Moreover, most of the droplet growth occurs in the evaporator section, and continues until the saturation ratio drops below 1. Once the saturation ratio drops below 1, the particles will start to evaporate. By truncating the warm wet-walled section the added water vapor is reduced, without affecting the peak supersaturation, or activation size. Note also that the time required for water evaporation for the non-hygroscopic particles of this model is about the same as for their growth. For the narrow tube diameter of these calculations (ID=2.5 mm) the residence time for droplet growth and evaporation (for non-hygroscopic particles) is just 0.04 seconds.

Figure 3:
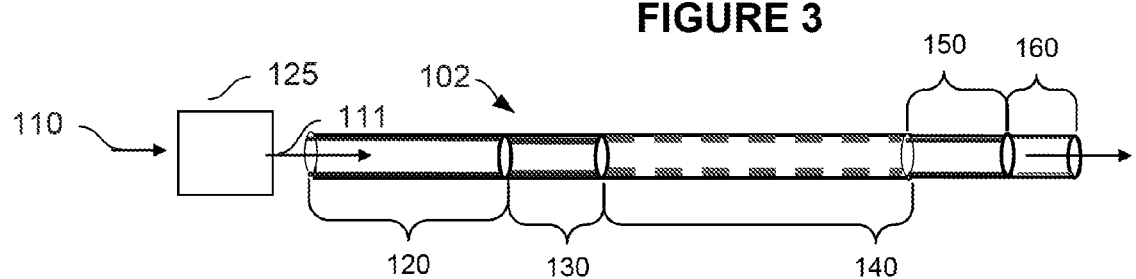
FIG. 3 shows a configuration of the nanoparticle condensation charger with two additional stages added for water vapor removal and temperature recovery.

FIG. 3 shows an alternate configuration of the condensation-evaporator 102 that incorporates active removal of water vapor. The purpose is to lower the water content of the air flow to allow the temperature of the exiting flow to be lowered, without producing condensation. In one implementation, this system adds a cooled wall section 150 to remove water vapor through condensation to the walls, and it adds a warm, dry-walled section 160 to restore the flow temperature. Other methods for removing water vapor commonly known in the field could be used, such as providing dessicant at the walls, or sheathing the flow with a dry air flow.

FIGS. 1 and 3 illustrate the ion source as positioned up-stream from the condensation evaporator, but in alternative embodiments the ions may be introduced between the initiator (130) and evaporator (140).

FIG. 4A illustrates a system condensation-evaporator for the nanoparticle charger, consisting of the inlet into which the particle laden flow and charging ions are introduced, and the conditioner, initiator, evaporator, water removal and temperature recovery sections which enlarge and then evaporate the particles.

FIG. 4A shows the construction of a condensation-evaporator following the multistage approach of FIG. 3. FIG. 4B is a cross sectional view along line A-A in FIG. 4A. The particle-laden flow passes through an ion source (not shown), and enters the condensation-evaporator at inlet 410. From there it passes through the five sections of the condensation-evaporator, namely the conditioner 420, initiator 430, evaporator 440, water removal 450, and temperature recovery 460. This specific system was designed for an air flow rate of 4.5 L/min. It consists of three parallel tubes (two tubes 412, 414 are illustrated in the cross section of FIG. 4B), each with an inner diameter of approximately 5 mm. The lengths of the conditioner 420, initiator 430, evaporator 440, water removal 450 and temperature recovery 469 sections are, respectively, 220 mm, 85 mm, 125 mm, 125 mm and 85 mm. The conditioner 420 and water removal section 450 are cooled by means of thermal electric devices. The initiator 430, evaporator 440 and temperature recovery 460 are heated either by contact film heaters or small heater cartridges. These temperatures are monitored using thermistors or thermal couples, and controlled using standardly available on-off or PID temperature controller circuitry.

FIG. 4B is a cross sectional view, showing two of the three tubes through which the flow passes. The walls of sections 420 and 430 are lined with a wick, constructed by rolling a piece of filter paper. In this construction, one wick spans both the conditioner and initiator sections. This wick is wetted by means of a small reservoir of water 470 located at the bottom of the initiator section 430. The lower end of the wick is mounted on a short standpipe that prevents the water from flowing through the wick and into the flow. A small thermistor is used to sense the water level, and triggers a water fill valve, which thereby maintains a fairly constant water level in the reservoir. The evaporator 440 has no wick, and has warm, dry walls. This is followed by the water removal section 460, which again has a wick in each tube to absorb the water that condenses from the air flow onto the walls. Each of the water removal wicks is mounted on a fluted standpipe which communicates with the small cavity 480. A small suction flow in the range of 2% to 10% of the total flow is connected at the base of the water removal standpipes to removes the condensed water from the system. The three flows are then joined in the section 460 tail piece which is heated to provide temperature recovery.

FIG. 5A shows the typical wall temperatures used in the operation and testing of the system of FIG. 4A, 4B. In this graph the axial position z is normalized with respect to the characteristic diffusion length $z\mathbf{0}=Q/D$, where D is the diffusion coefficient for water vapor and Q is the volumetric flow rate. The axial positions corresponding to each of the five sections (conditioner, initiator, evaporator, water removal and temperature recovery) are labeled. As indicated, the conditioner spans the axial evaporator extends over $0.04<z/z\mathbf{0}<0.21$, water removal over $0.21<z/z\mathbf{0}<0.32$ and temperature recovery to $0.32<z/z\mathbf{0}<0.4$. The wall temperatures of the conditioner and initiator are nominally set at 2° C. and 35° C. respectively, but the model also includes short temperature ramps from the ambient conditions and between the successive sections. For reasons of construction, the evaporator has two temperature regions, one at the initiator temperature of 35° C. (corresponding to the standpipe) and a longer one at 45° C. The water removal and temperature recovery sections are at 8° C. and 28° C.

FIG. 5B shows, for the scenario of FIG. 5A, the saturation ratios calculated for flow trajectories along the centerline (solid line, r/Ro=0) and at a radial position equal to 70% of the tube radius (r/Ro=0.7, dashed line) where r is the radial position, and Ro is the tube radius. For this geometry and these operating conditions the maximum saturation ratio value is about 1.4, which is sufficient to activate the condensational growth of particles roughly 5 nm in diameter. Because of the energy associated with surface tension, the equilibrium vapor pressure over the curved surface of the droplet is higher than over a flat surface of the same chemical composition, thus requiring greater than 100% RH values to initiate the condensational growth. This dependence varies as the inverse of the particle diameter, as described by the Kelvin relation. As shown in FIG. 5B, the axial position of the maximum saturation depends on the radial position, with those trajectories closer to the tube wall achieving their maximum sooner (i.e. at lower axial positions) than along the centerline. This is typical of convective diffusion, where the transport of water vapor from the warmed walls of the initiator to the centerline takes more time, due to the longer transport distance, and this greater time corresponds to a larger axial position. In fact, with this configuration the centerline saturation ratio reaches its maximum in the evaporator section.

Figure 5A:
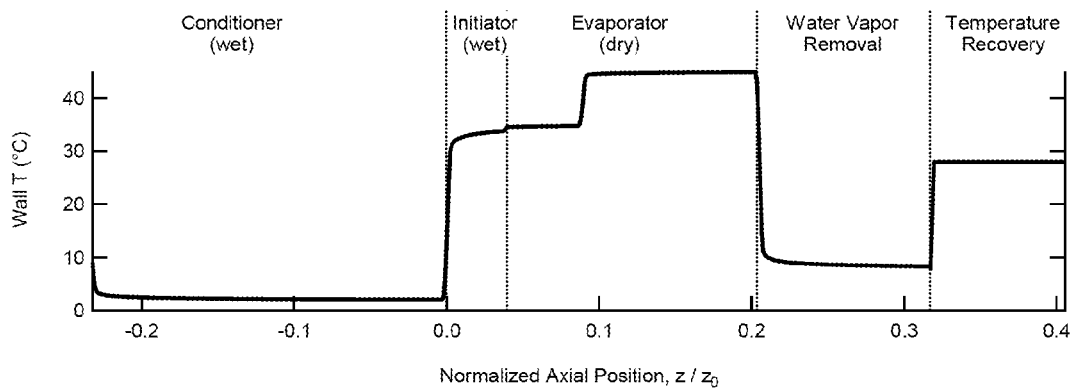
FIG. 5A shows the typical wall temperatures used in the operation and testing of the system of FIG. 4A.
Figure 5B:
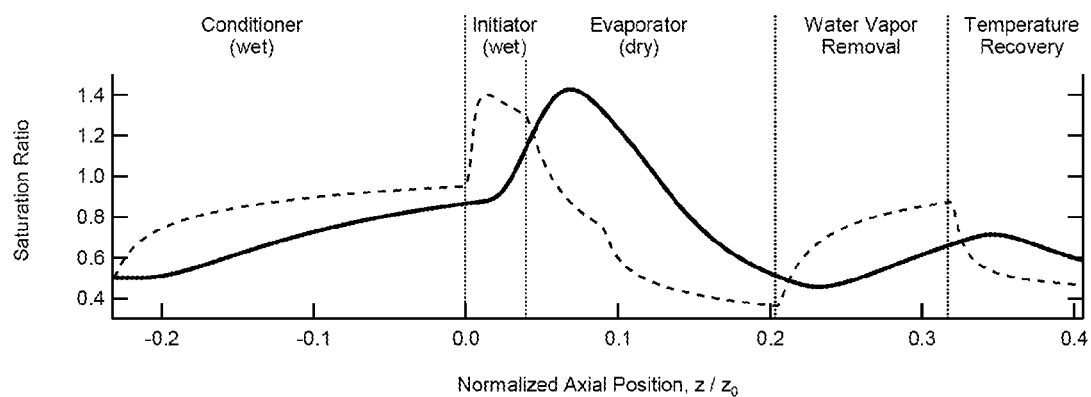
FIG. 5B shows, for the scenario of FIG. 5A, the saturation ratios calculated for flow trajectories along the centerline.
Figure 5C:
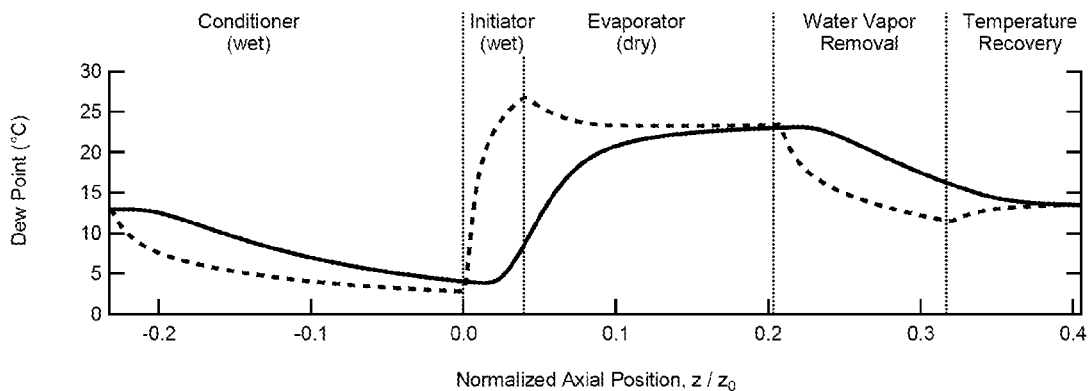
FIG. 5C shows, for the scenario of FIG. 5A, the dew point values calculated for flow trajectories along the centerline.

FIG. 5C shows, for the scenario of FIG. 5A, the dew point values calculated for flow trajectories along the centerline (solid line) and at the radial position equal to 70% of the tube radius (dashed line). Although the relative humidity exiting the evaporator along these trajectories is between 4%-50%, the dew point is about 23° C. This means that the water content is sufficient to produce condensation if the flow is cooled to a typical ambient or room temperature of 20° C. For many applications it is desired to reduce this dew point, so that the downstream components do not need to be heated. This is accomplished through the water removal section, which has cooled walls. By appropriately selecting the length of this section, and relying on the fast diffusion of water vapor, it is possible to reduce the dew point to around 13°-14° C., without saturating the flow (except at the walls themselves).

Figure 6:
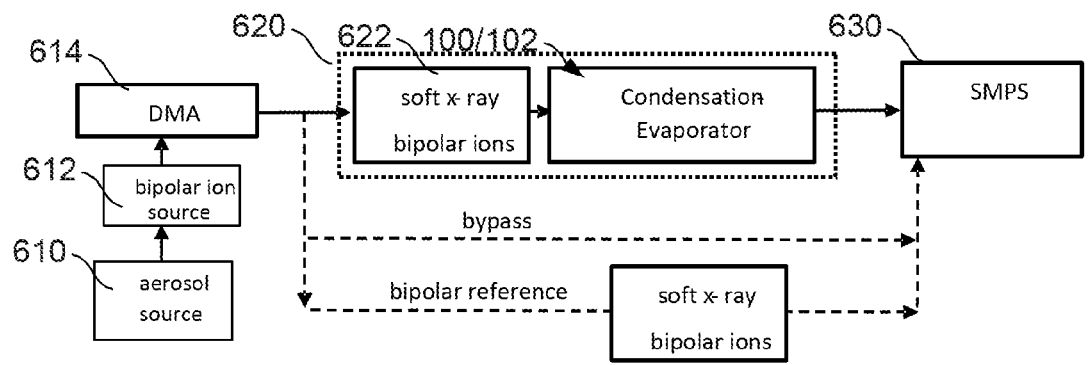
FIG. 6 illustrates the experimental configuration used to measure the charging efficiency and charge distribution produced by a condensation-evaporator nanoparticle charger.
Figure 7A:
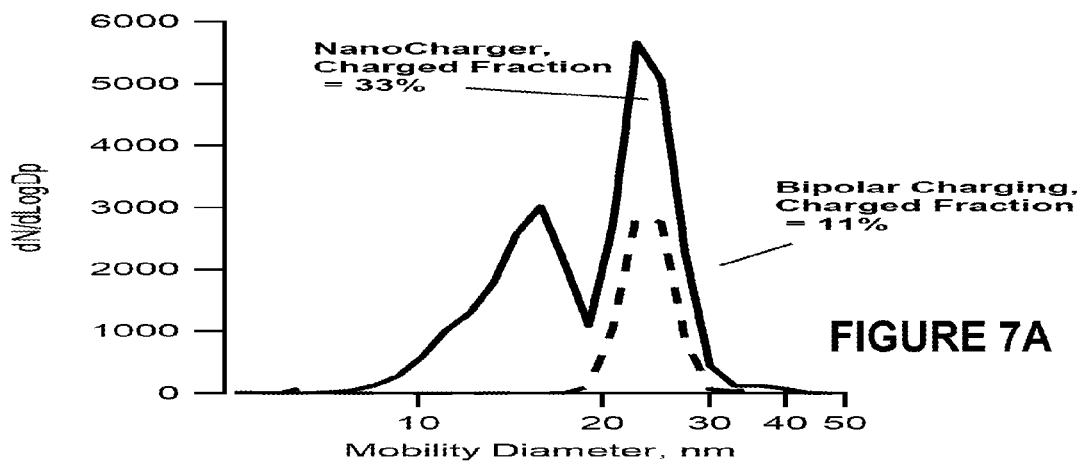
FIG. 7A shows the mobility distribution output by the nanoparticle charger of the configuration shown in FIG. 1 using a bipolar ion source, when presented with a test aerosol is centered at 25 nm.
Figure 7B:
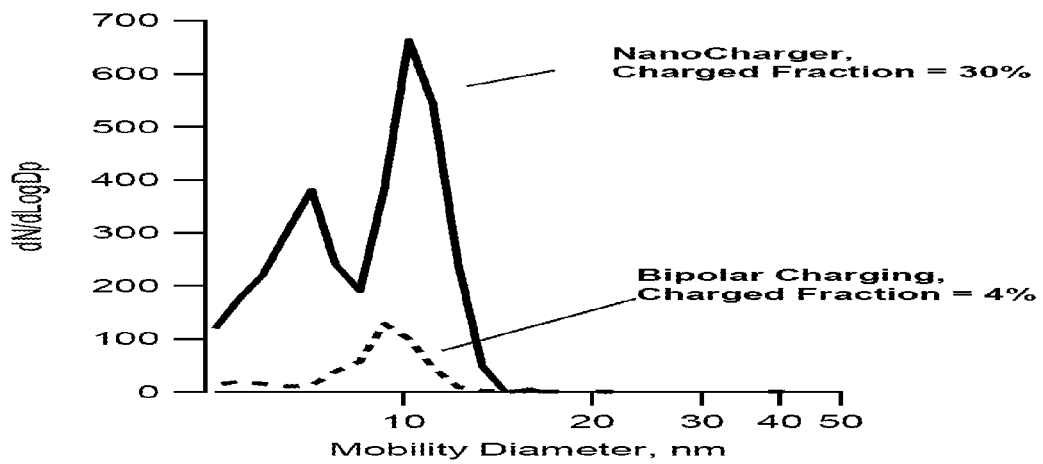
FIG. 7B shows the mobility distribution obtained with the system of FIG. 7A for an input aerosol centered at 10 nm.

FIG. 6 is an experimental configuration used to measure the charging efficiency and charge distribution produced by a condensation-evaporator nanoparticle charger, and shows the differential mobility analyzer (DMA 614) used to size-select the monodisperse test particles, the nanoparticle charger consisting of the bipolar ion source and condensation-evaporator, and the scanning mobility particle sizing system (SMPS 630) used to measure the resulting distribution in particle mobilities.

The efficacy of the condensation-evaporator nanoparticle charger was tested using a bipolar ion source coupled to the inlet of the condensation-evaporator, as shown in FIG. 6. As is commonly established aerosol technology, testing was done with size-classified, monodisperse particles. Particles spanning a range of particle sizes are generated using an aerosol source 610, such as a furnace or atomizer. These polydisperse particles pass through a bipolar ion source 612, where they acquire a steady-state, or equilibrium electrical charge distribution. As is well known in the field, this bipolar ion source provides both negatively and positively charged particles (in addition to the uncharged particles), but minimizes the number of multiply charged particles. Next the particles are size-classified using a differential mobility analyzers (DMA) 614, which selects particles of a single polarity and electrical mobility based on the transit time and electric field within the mobility analyzer. These monomobility particles were then passed through a nanoparticle charger consisting 620 of a soft X-ray bipolar ion source 622 (TSI Model 3087, Shoreview, Minn.) and a condensation-evaporator 100 or 102. The electrical mobility of the positively charged particles exiting the nano-charger was measured using a second mobility analyzer 630 operated in scanning mode, commonly referred to as an SMPS. The mobility distribution of the positively charged particles output by the nanoparticle charger provides the total number of positively charged particles as a function of the number of charges per particle. The overall efficiency for charging is determined by comparison to SMPS measurements upstream of the nanoparticle charger, as measured on the "bypass" line of FIG. 6. For comparison to established bipolar charging methods, measurements are also made using the bipolar ion source alone, without the condensation evaporator, as shown by the "bipolar reference" line of FIG. 6.

The first set of experiments used a system of like that shown in FIG. 1, where the ion source was coupled to a condensation-evaporation system without a water removal system. The bipolar ion source was provided by the soft-Xray source (TSI Model 3087). The condensation evaporator 100 used a conditioner, initiator, and evaporator measuring 116 mm, 70 mm and 112 mm in length, respectively. The system had three parallel tubes, with an inner diameter of 0.18 inches. No water removal section was employed. The wall temperatures were 5° C., 26° C. and 32° C. for the conditioner, initiator and evaporator, respectively. The system was operated at 4.5 L/min air flow with an initiator-dryer residence time of 140 ms.

FIG. 7A shows the mobility distribution output by the nanoparticle charger of the configuration shown in FIG. 1 using a bipolar ion source, when presented with a test aerosol is centered at 25 nm. Singly charged 25 nm particles appear at a mobility size of 25 nm, while multiply charged particles, being more mobile, appear at smaller mobility diameters. The mobility distribution for simple, bipolar charging is also shown.

FIG. 7A shows the mobility distribution measured for a input particle size centered at 25 nm that has passed through the nano-charger (solid line), or through a traditional bipolar ion source (dashed line). The abscissa of this graph expresses the measured mobility as the diameter of a singly charged particle of the same mobility. Singly charged particles of the selected upstream DMA size appear at that same mobility size in the downstream size distribution. Doubly charged particles, being more mobile, appear at a smaller mobility size. For particles that passed through the bipolar ion source only, a unimodal mobility peak centered at the input particle size of 25 nm is seen, and the fraction of those particles sampled that are positively charged is 11%. This is as predicted by the Fuchs relations for particle charging. For particles that passed through the nano-charger, consisting of the same bipolar ion source followed by the condensation-evaporator, the fraction of particles carrying a positive charge increases to 33%. Of these, just over one-half of the charged particles carry a single charge, about one-third are doubly charged, and a few are triply charged. Because the ion source used is bipolar, an approximately equal number of particles will be negatively charged, bringing the total charged fraction to about 60-65%.

FIG. 7B shows results for the same system for an input particle size centered at 10 nm. As for the 25 nm test particles, those particles that passed through the bipolar ion source only, exhibit unimodal mobility peak centered at the input particle size of 10 nm, indicating the presence of singly charged particles only. However, at this smaller size the fraction of those particles sampled that acquire a positive charge is ~5%. This is significantly lower than at 25 nm, and is consistent with theoretical predictions for bipolar charging. Those particles that passed through the nano-charger, again consisting of the same bipolar ion source followed by the condensation-evaporator, the fraction of positively particles charged increases to 30%. This is close to the value obtained at 25 nm. As before, just over one-half of the charged particles produces by the nano-charger carry a single charge, and the remaining are mostly doubly charged. While the efficiency for acquiring charge using bipolar ions decreases dramatically for the smaller particles, with the bipolar ions coupled to the condensation-evaporator, the charging efficiency is essentially the same for both input particle sizes, with a value near 30%. Additionally, most charged particles carry just one net charge.

FIG. 8A shows the mobility distribution output by the nanoparticle charger of the configuration shown in FIG. 4 using a bipolar ion source, when presented with a test aerosol is centered at 20 nm. Singly charged 20 nm particles appear at a mobility size of 20 nm, while multiply charged particles, being more mobile, appear at smaller mobility diameters. The mobility distribution for simple, bipolar charging is also shown. FIG. 8B shows the mobility distribution obtained with the system of FIG. 8A for an input aerosol centered at 10 nm. For the data shown the operating temperatures were 2° C., 35° C., 45° C., 8° C. and 28° C. for the conditioner, initiator, evaporator, water removal and temperature recovery stages. The flow through the system was 4.5 L/min, and the sampled air was dry, at ~25° C.

Figure 4A:
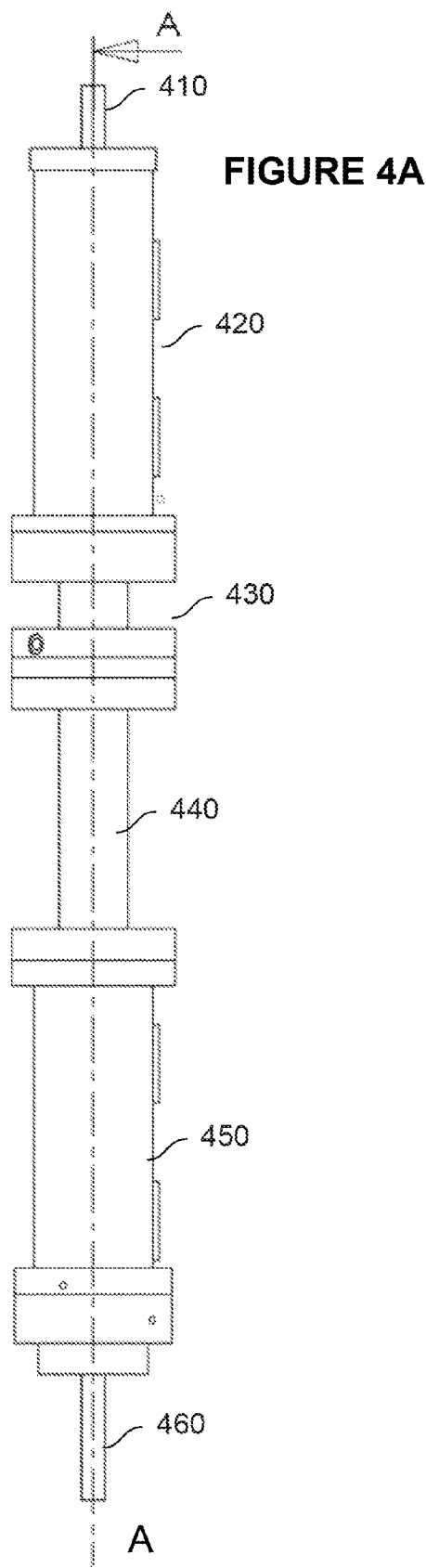
FIG. 4A illustrates a system condensation-evaporator for the nanoparticle charger.
Figure 4B:
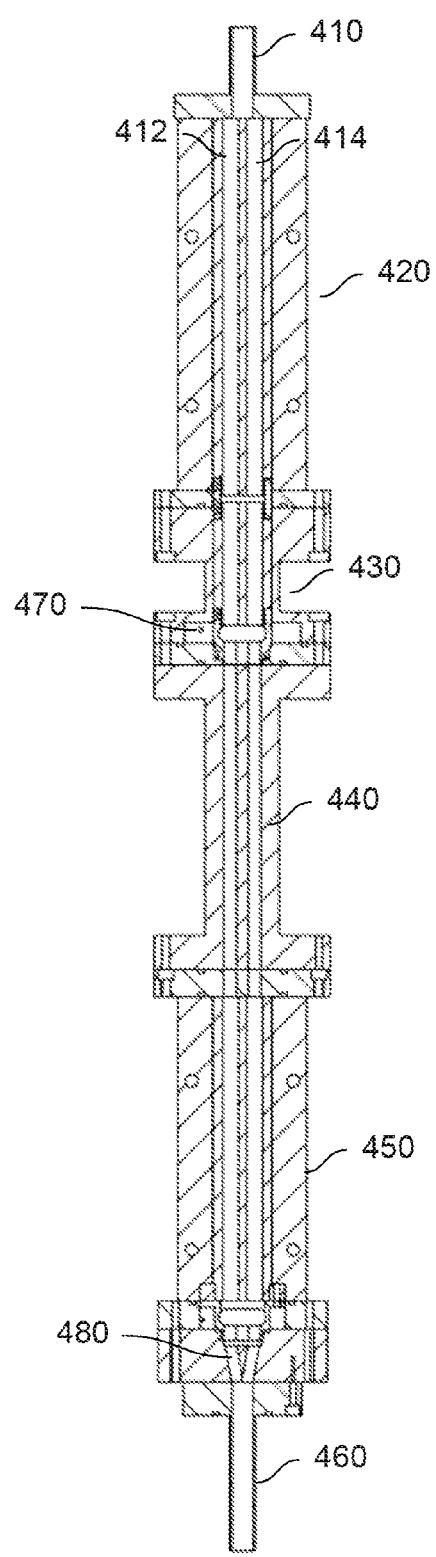
FIG. 4B is a cross sectional view of the system of FIG. 4A, showing two of the three parallel tubes used for particle growth and evaporation.

FIG. 8B shows the mobility distribution output by the nanoparticle charger of the configuration shown in FIG. 4 using a bipolar ion source, when presented with a test aerosol is centered at 10 nm. Singly charged 10 nm particles appear at a mobility size of 20 nm, while multiply charged particles, being more mobile, appear at smaller mobility diameters.

Figure 8A:
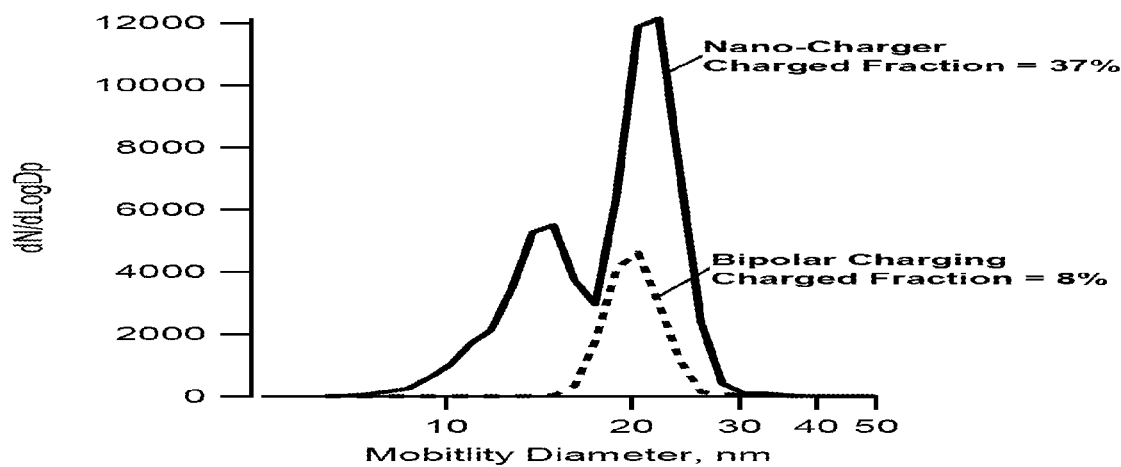
FIG. 8A shows the mobility distribution output by the nanoparticle charger of the configuration shown in FIG. 4 using a bipolar ion source, when presented with a test aerosol is centered at 20 nm. Singly charged 20 nm particles appear at a mobility size of 20 nm, while multiply charged particles, being more mobile, appear at smaller mobility diameters. The mobility distribution for simple, bipolar charging is also shown.
Figure 8B:
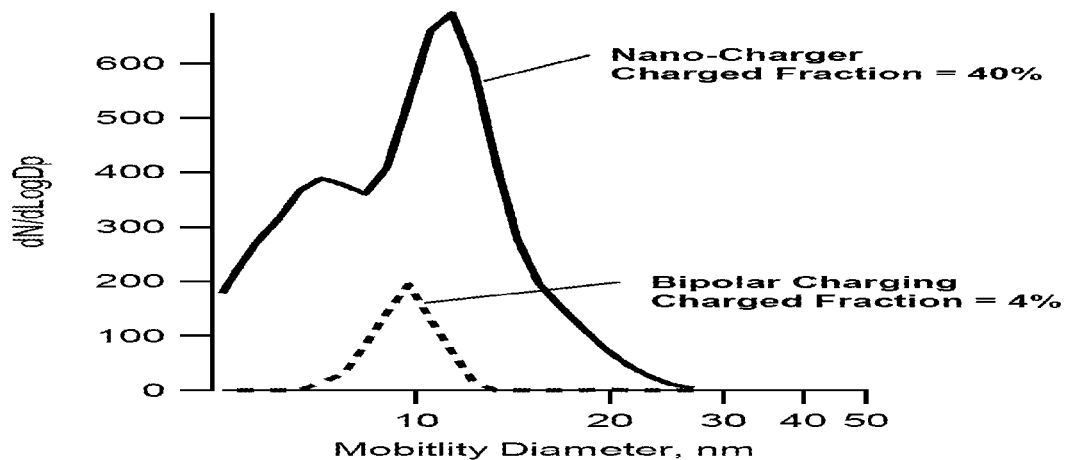
FIG. 8B shows the mobility distribution obtained with the system of FIG. 8A for an input aerosol centered at 10 nm.

FIGS. 8A and 8B show results for the system of FIG. 4, where a water removal and temperature recovery stages have been added to the system. With the additional stages, it is possible to operate at a larger temperature for the initiator, without producing condensation once the exiting flow is returned to room temperature. This higher temperature difference between the initiator and the conditioner provides a higher supersaturation, which activates to smaller particle sizes and produces somewhat larger droplets. The result is a somewhat higher charging efficiency. As shown in FIGS. 8A and 8B, with this configuration the efficiency for placing positive charges onto the particles is close to 40% at both 10 nm and 20 nm. Approximately 60% of those charged carry a single net charge. By comparison, the efficiency for bipolar charging is 4% at 10 nm, and 8% at 20 nm.

In summary, a condensation-evaporation system has been designed for use with an ion source to provide more efficient charging of nanometer-sized particles than is possible through direct exposure to an ion source. In tests with a bipolar ion source, this nano-charger provides charging efficiencies of the order of 30% to 40% for a single polarity. An equal fraction of particles of the opposite polarity will be charged, leading to a total charge fraction of 60-80%. Of those particles that are charged, approximately 60% carry a single net charge, with the remaining fraction carrying two or more charges. The fraction of charged particles is found to be independent of the input particle size. Yet higher charging efficiencies may be achieved if the bipolar ion source were replaced with a unipolar ion source, however this may lead to a higher proportion of more highly charged individual particles.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A particle charging apparatus, comprising:

an ion source; and a container having at least one wick to provide wetted walls into which an air flow is introduced in a laminar manner, said container having at least a first section, a second section and a third section, the first section including the wetted walls at a first temperature T1, the second section adjacent to the first section and having the wetted walls at a second temperature T2 greater than the first temperature T1, the third section adjacent to the second section and having dry walls provided at a temperature T3 greater than T2, the temperature T3 being higher than a condensation point of the flow entering the third section.

2. The particle charging apparatus of claim 1 wherein the air flow passes through both the ion source and the container.

3. The particle charging apparatus of claim 1 wherein the ion source is positioned to output the air flow to an input to the first section.

4. The particle charging apparatus of claim 1 wherein the ion source is bipolar.

5. The particle charging apparatus of claim 1 wherein the ion source is unipolar.

6. The particle charging apparatus of claim 1 further including a fourth section of the container having walls at a temperature T4 cooler than T2 and T3.

7. The apparatus of claim 6 further including a fifth section of the container having dry walls operated at a temperature T5 greater than the temperature T4.

8. A nanoparticle charger apparatus, comprising:

an ion source;

a container having at least one wick to provide wetted walls into which an air flow is introduced in a laminar manner, said container having at least a first section, a second section, a third section, and a forth section the first section including the wetted walls at a first temperature T1, the second section adjacent to the first section and having the wetted walls at a second temperature T2 greater than the first temperature T1, the third section adjacent to the second section and having dry walls provided at a temperature T3 greater than T2 and the temperature T3 being higher than a condensation point of the flow entering the third section, the fourth section operated at a temperature T4 selected to remove water vapor from the flow.

9. The particle charging apparatus of claim 8 wherein temperature T4 is warmer than T1 and cooler than T2 and T3.

10. The apparatus of claim 8 wherein the air flow includes a carrier gas and a particle laden flow.

11. The apparatus of claim 10 wherein the carrier gas is air.

12. The particle charging apparatus of claim 8 wherein the air flow passes through both the ion source and the container.

13. The particle charging apparatus of claim 12 wherein the ion source is positioned to output the air flow to an input to the first section.

14. The particle charging apparatus of claim 13 wherein the ion source is bipolar.

15. The particle charging apparatus of claim 13 wherein the ion source is unipolar.

16. A method of electrically charging particles, comprising:

providing a container having at least one wick to provide wetted walls into which a particle laden flow may be introduced, having at least a first section, a second section adjacent to the first section and a third section adjacent to the second section;

passing the particle laden flow through an ion source;

introducing the particle laden flow into the container in a laminar manner; and operating the first section with wetted walls at a first temperature T1, the second section at a second temperature T2 greater than the first temperature T1, and the third section with dry walls at a temperature T3 greater than T2, and the temperature T3 being higher than a condensation point of the flow entering the third section.

17. The method of claim 16 wherein the step of passing occurs prior to the step of introducing.

18. The method of claim 16 further including providing a fourth section adjacent to the third section and operating the fourth section at a temperature cooler than T2 and T3.

19. The method of claim 18 further including providing a fifth section adjacent to the fourth section and operating the fifth section at including a fifth section at a temperature T5 greater than the temperature T4.

* * * * *